United States Patent [19]
Mattisson et al.

[11] Patent Number: 5,792,367
[45] Date of Patent: Aug. 11, 1998

[54] SYSTEM AND METHOD FOR MONITORING A FLOW OF DIALYSIS FLUID IN A DIALYSIS MACHINE

[75] Inventors: Leif Mattisson, Sodra Sandby; Gunilla Wejfeldt, Lund, both of Sweden

[73] Assignee: Gambro AB, Sweden

[21] Appl. No.: 693,263

[22] PCT Filed: Feb. 17, 1995

[86] PCT No.: PCT/SE95/00166

§ 371 Date: Aug. 16, 1996

§ 102(e) Date: Aug. 16, 1996

[87] PCT Pub. No.: WO95/22743

PCT Pub. Date: Aug. 24, 1995

[30] Foreign Application Priority Data

Feb. 18, 1994 [SE] Sweden .................... 9400555

[51] Int. Cl.⁶ .................... B01D 61/30; B01D 65/10
[52] U.S. Cl. .................... 210/741; 73/865.9; 210/87; 210/90; 210/646; 210/929; 364/510; 604/4
[58] Field of Search .................... 210/85, 87, 90, 210/143, 321.65, 433.1, 637, 646, 739, 741, 742, 929; 604/4–6; 364/500, 502, 510; 73/1.01, 1.16, 1.57, 38, 40, 865.9

[56] References Cited

U.S. PATENT DOCUMENTS

| | | | |
|---|---|---|---|
| 4,370,983 | 2/1983 | Lichtenstein | 210/929 |
| 4,585,552 | 4/1986 | Gummesson et al. | 210/87 |
| 4,762,618 | 8/1988 | Gummeson et al. | 210/646 |
| 5,342,527 | 8/1994 | Chevallet et al. | 210/646 |
| 5,580,460 | 12/1996 | Polaschegg | 210/646 |

FOREIGN PATENT DOCUMENTS

| | | |
|---|---|---|
| 0204174 | 12/1986 | European Pat. Off. |
| 0298587 | 1/1989 | European Pat. Off. |
| 0565485 | 10/1993 | European Pat. Off. |
| 0579559 | 1/1994 | European Pat. Off. |
| 2003274 | 3/1979 | United Kingdom |

OTHER PUBLICATIONS

J. Phys. E: Sci. Instrum., vol. 15, 1982, T J S Brain et al., "Survey of pipeline flowmeters" pp. 968–971.

Technisches Messen tm. vol. 52, No. 1, 1985, D. Meyer et al., "Erfahrungen beim Einsatz von Durchfluss–und Mengenmessern in der chemischen Industrie," pp. 13–14.

*Primary Examiner*—Joseph W. Drodge
*Attorney, Agent, or Firm*—Lerner, David, Littenberg, Krumholz & Mentlik

[57] ABSTRACT

Apparatus for monitoring flow of a dialysis fluid through a dialyzer is disclosed including a computer for calculating the flow rate of the dialysis fluid into and out of the dialyzer based on the formula $P-P_O = k*Q^n$ in which P is the pressure in the dialysis fluid between a throttle and a pump either upstream or downstream of the dialyzer, $P_O$ is the pressure in the dialysis fluid on the opposite side of the throttles from the pump, k is a characteristic coefficient for the throttle, Q is the flow of the dialysis fluid through the throttle, and N is a characteristic exponent for the throttle, and the apparatus includes microprocessor for calculating the values of k and $P_O$ prior to use and for calculating the value of $P_O$ during use of the dialyzer. Methods for carrying out such monitoring are also disclosed.

11 Claims, 2 Drawing Sheets

SYSTEM AND METHOD FOR MONITORING A FLOW OF DIALYSIS FLUID IN A DIALYSIS MACHINE

FIELD OF THE INVENTION

The present invention relates to a system and method for monitoring a fluid flow in a dialysis machine. More specifically, the present invention relates to a back-up system for monitoring the correct operation of dialysis fluid flow rates and/or ultrafiltration volume measurements in a dialysis machine.

BACKGROUND OF THE INVENTION

The present invention is described below in relation to a known dialysis machine, namely the GAMBRO AK-100. Such a dialysis machine is described, for example, in European Patent Nos. B1-0 204,174 and B1-0 204,260.

The dialysis machine comprises a first part for preparing, mixing and conditioning a dialysis fluid, and a second part for supplying the fluid to a dialyzer and for controlling and monitoring the flow. The second part comprises two constant flow regulators positioned upstream and downstream, respectively, of the dialyzer.

Each flow regulator comprises a restrictor, a pressure sensor and a pump. The pressure sensor controls the pump in such a way that the pressure between the restrictor and the pump remains substantially constant. Since the inlet pressure upstream of the one throttle device and the outlet pressure downstream of the other restrictor or throttle device is substantially constant, a constant pressure drop over the respective restrictor is obtained, which means that there is a constant flow therethrough.

In hemodialysis, hemofiltration and hemodiafiltration an amount of fluid is separated from the blood flow by the filter which is used. This means that the flow downstream of the filter will be somewhat larger than the flow upstream of the filter. This ultrafiltration is adjusted by the above-referenced flow regulators. There are also other ways of achieving ultrafiltration, for example by adjusting the flow regulators to the same value and removing a separate ultrafiltration flow by means of a separate pump.

The remaining elements of this dialysis machine are disclosed in the aforesaid European Patent No. B1-0 204,174, to which reference is now made, and the disclosure of this is incorporated herein by reference thereto.

The adjustment and regulation of the dialysis machine is described in more detail in European Patent No. B1-0 204,260. Briefly, adjustment implies that a desired ultrafiltration is set by electrical adjustment devices. Additionally, a desired flow rate is set for the dialysis fluid, for example 300 ml/minute, 500 ml/minute or 700 ml/minute. The set values are supplied to a regulating computer which calculates and/or supplies set values for pressure in the pressure sensors of the flow regulators. The pressure set values are then continually adjusted in the regulating computer depending on the measured values of flow which are obtained in a separate flow measurement arrangement.

Generally, the regulating computer includes a first feed-back loop from the pressure sensors to the pumps.

Moreover, the regulating computer includes the pressure sensors in a second feed-back regulating loop maintaining the pressure at the desired value.

The first feed-back loop has a fast response and thus immediately compensates for any possible variations in the pressure, as well as any possible pressure surges in the system. The change of the set values for the pressure sensors in the second feed-back loop takes place slower.

In order to increase the safety of the system in the dialysis machine, two separate microcomputers are used, one monitoring computer and one regulating or controlling computer. Further characteristics of the adjustment arrangement are disclosed in the aforesaid European Patent No. B1-0 204,260.

The accuracy of the aforesaid system is dependent on the measurement accuracy of the flow measurement device. This flow measurement device is basically constructed as is disclosed in either of British Patent No. 2,003,274 or European Patent No. B1-0 106,940.

The measurement device consists of two measuring cells, through which fluid flows pass into and out of the dialyzer. There is a magnetic field perpendicular to the measuring cells and platinum electrodes are in contact with the fluid flow. Voltages are generated between the electrodes due to the flow of fluid comprising ions in the magnetic field, said voltages being proportional to the flows.

Such a measuring device is, however, prone to operational problems, such as deposits on the measurement electrodes, which can result in measurement error. This problem is described in U.S. Pat. Nos. 4,585,552 and 5,261,283, along with methods for avoiding or minimizing this problem.

In order to monitor the ultrafiltration, the transmembranal pressure TMP of the dialyzer is used in the GAMBRO AK 100 dialyzer. The monitoring computer checks that the transmembral pressure TMP lies within the allowed range after the pressure has stabilized. The ratio between the ultrafiltration rate and the transmembral pressure forms an ultrafiltration-coefficient, or UF-coefficient, with the help of which the actual ultrafiltration can be calculated. Such a calculation must however take account of the oncotic pressure (osmotic pressure caused by plasma proteins), and the spread of the UF-coefficient for the actual type of dialyzers, as well as the fact that the UF-coefficient decreases during the treatment. It can be difficult to set an allowable range for the transmembranal pressure TMP which is sufficiently large to avoid false alarms and which is sufficiently narrow such that the corresponding range of the UF-rate will not be too large. As is clear, it can be difficult to obtain accurate measurement of the accumulated ultrafiltration volume by means of TMP, and it is only used for back-up control purpose.

SUMMARY OF THE INVENTION

In accordance with the apparatus of the present invention, the inventors have discovered apparatus for monitoring the flow of a dialysis fluid through a dialysis machine comprising a dialyzer, the apparatus comprising first constant flow means for feeding the dialysis fluid to the dialyzer, second constant flow means for withdrawing the dialysis fluid from the dialyzer, the first constant flow means comprising a first throttle, a first pump, and a first pressure sensor for sensing the pressure in the dialysis fluid between the first throttle and the first pump, the second constant flow means comprising a second throttle, a second pump, and a second pressure sensor for sensing the pressure in the dialysis fluid between the second throttle and the second pump, pump control means for controlling the first and second pumps in order to maintain a substantially constant flow of the dialysis fluid through the first and second pumps based upon the pressures measured by the first and second pressure sensors, first flow measurement means for measuring the flow of the dialysis fluid into the dialyzer, and second flow measurement means for measuring the flow of the dialysis fluid out of the dialyzer, the apparatus also including calculating means for calculating the flow rates of the dialysis fluid into and out of the dialyzer based upon the formula $P-O_O=k*Q^n$, wherein P comprises the pressure in the dialysis fluid between the first throttle and the first pump or the pressure in the dialysis fluid between the second throttle and the second pump, $P_O$ comprises the pressure in the dialysis fluid on the opposite side of the first throttle or the second throttle, k comprises a characteristic coefficient for the first throttle or the second throttle, Q comprises the flow of the first dialysis fluid through the first throttle or the second throttle, and n comprises a characteristic exponent for the first throttle or the second throttle, and calibration means for calibrating the value of k and $P_O$ prior to use of the dialysis machine based upon the flow of the dialysis fluid measured by the first and second flow measurement means, and for calibrating the value of $P_O$ during the use of the dialysis machine, including decoupling means for decoupling the dialyzer from the apparatus whereby the value of $P_O$ can be calculated during use of the dialysis machine by the flow of the dialysis fluid measured by the first and second flow measurement means.

In accordance with one embodiment of the apparatus of the present invention the first pump is disposed closer to the dialyzer than the first throttle, and the second pump is disposed closer to the dialyzer than the second throttle.

In accordance with another embodiment of the apparatus of the present invention the value of n is approximated to a predetermined value, and preferably the predetermined value is 2.

In accordance with another embodiment of the apparatus of the present invention the apparatus includes temperature measuring means for measuring the temperature of the dialysis fluid whereby the values of k and $P_O$ can be corrected based upon the temperature of the dialysis fluid measured by the temperature measuring means.

In accordance with another embodiment of the apparatus of the present invention the value of $P_O$ is initially approximated to a constant predetermined value, and in a preferred embodiment the constant predetermined value comprises atmospheric pressure.

In accordance with the present invention the inventors have also discovered a method for monitoring the flow of a dialysis fluid through a dialysis machine comprising a dialyzer, first constant flow means for feeding the dialysis fluid to the dialyzer, second constant flow means for withdrawing the dialysis fluid from the dialyzer, the first constant flow means comprising a first throttle, a first pump, and a first pressure sensor for sensing the pressure in the dialysis fluid between the first throttle and the first pump, and the second constant flow means comprising a second throttle, a second pump, and a second pressure sensor for sensing the pressure in the dialysis fluid between the second throttle and the second pump, the method comprising feeding the dialysis fluid through the dialyzer by the first constant flow means, withdrawing the dialysis fluid from the dialyzer through the second constant flow means, maintaining a substantially constant flow of the dialysis fluid through the first and second pumps based upon the pressures measured by the first and second pressure sensors, measuring the flow of the dialysis fluid into the dialyzer, measuring the flow of the dialysis fluid out of the dialyzer, calculating the flow rates of the dialysis fluid into and out of the dialyzer based upon the formula $P-P_O=k*Q^n$, wherein P comprises the pressure in the dialysis fluid between the first throttle and the first pump or the pressure in the dialysis fluid between the second throttle and the second pump, $P_O$ comprises the pressure in the dialysis fluid on the opposite side of the first throttle or the second throttle, k comprises a characteristic coefficient for the first throttle or the second throttle, Q comprises the flow of the dialysis fluid through the first throttle or the second throttle, and n comprises a characteristic exponent for the first throttle or the second throttle, and calibrating the value of k and $P_O$ prior to use of the dialysis machine based upon the flow of the dialysis fluid into and out of the dialyzer, and for calibrating the value of $P_O$ during use of the dialysis machine, including decoupling the dialyzer from the apparatus whereby the value of P can be calculated during use of the dialysis machine by the flow of the dialysis fluid into and out of the dialyzer.

In accordance with one embodiment of the method of the present invention the method includes calibrating at least the values of k and $P_O$ comprising feeding an increased flow of fluid through at least one of the first and second throttles, measuring the pressure of at least one of the first and second pressure sensors during the increased flow, and measuring the flow of the dialysis fluid into and out of the dialyzer during the increased flow.

In accordance with another embodiment of the method of the present invention the method includes calibrating at least the value of $P_O$ comprising feeding at least a first increased large flow and a second increased large flow differing from the first increased large flow to at least one of the first and second throttles, measuring the flow into or out of the dialyzer during the first and second increased flows, and calculating the value of $P_O$ based thereon.

In accordance with another embodiment of the method of the present invention the method includes calculating the accumulated ultrafiltration in the dialysis machine based upon the flow of the dialysis fluid into and out of the dialyzer and the measured flows of the dialysis fluid through the first and second throttles.

From the above discussion it can be readily seen that it is desirable to further monitor the dialysis machine in order to be sure that the correct values are obtained for the flow, and in particular for the flow difference in order to monitor the ultrafiltration rate and volume. Such an extra monitoring step can also be used in order to indicate when the flow measurement arrangement has to be cleaned, changed or taken care of in some other way in order to provide the correct and confident measured values. Such monitoring can further be used in order to provide an alarm signal in the event of suspected error conditions.

From the above it is also clear that such a dialysis device already comprises a throttle device and a pressure sensor which essentially detects the pressure drop over the throttle device. It is known that the pressure drop over the throttle device is approximately proportional to the square of the flow, i.e.

$$P-P_O=k*Q^n$$

where P is a pressure on one side of the throttle device, $P_O$ is a back pressure on the other side of the throttle device, k is a characteristic coefficient for the throttle device, Q is the flow through the throttle device and n is the characteristic exponent of the throttle device, normally equal to about 2.0.

According to the present invention the measured value P for pressure on one side of the throttle device is used, that value already being available in the regulating computer, in order to calculate the flow through the throttle device by means of the aforementioned equation. The flow thus calculated is compared with the measured value which is obtained from the above mentioned flow measurement device. If the difference between the calculated value and the measured value exceeds a predetermined value, suitable precautions are taken, for example generating an alarm signal.

For practical purposes it has been found that the exponent n in the above-mentioned equation can be approximated to two, i.e. a quadratic relationship exists between pressure and flow. The error of such an approximation is relatively small and can be compensated for, as will be described below.

The coefficient k is dependent on the geometry of the throttle device and is determined experimentally.

The coefficient k is somewhat dependent on the temperature and can be corrected by means of the measured temperature. The temperature value of the dialysis fluid is normally in the regulating computer.

The back pressure $P_O$ can be estimated, but is preferably also determined experimentally. The back pressure can also be used to compensate for the small variations between the real situation and the aforementioned theoretical model.

In the aforesaid dialysis machine, the pressure sensor measures pressure (P) between the throttle device and the pump, whereby it is a condition that the back pressure ($P_O$) on the other side of the throttle device is constant, for example equal to atmospheric pressure. If this is not the case, a differential pressure meter is preferably used, which measures the pressure difference over the throttle device. Alternatively, a second pressure sensor can be used to measure the back pressure.

Further objects, advantages and features of the present invention will become evident from the following description of a preferred embodiment with reference to the appended drawings.

DETAILED DESCRIPTION

Figure 1:
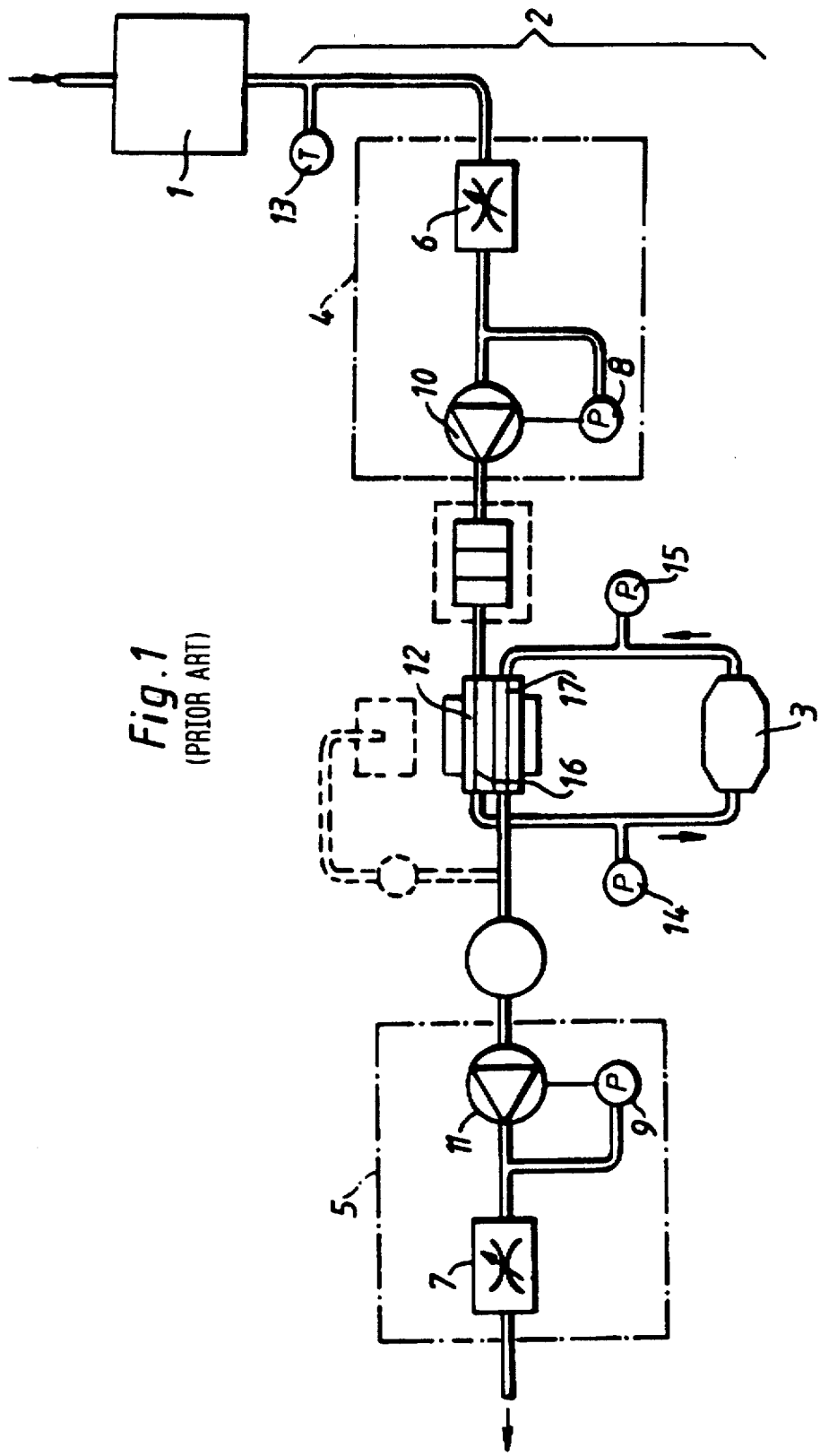
FIG. 1 is a schematic representation of a flow diagram for a known dialysis machine corresponding to the dialysis machine GAMBRO AK-100.

Referring to the figures, in which like reference numerals refer to like elements thereof, FIG. 1 shows a basic partial flow diagram for the GAMBRO AK-100 dialysis machine. This dialysis machine comprises a first part 1 for mixing and conditioning the dialysis fluid and a second part 2 for supplying the fluid to a dialyzer 3. Part 1 is described in detail in European Patent No. B1-204,174, mentioned above.

In the second part there are two constant flow regulators 4 and 5 positioned upstream and downstream, respectively, of the dialyzer 3, as seen in the direction of flow of the dialysis fluid.

Each flow regulator comprises a restrictor, 6 or 7, a pressure sensor, 8 or 9, as well as a pump, 10 or 11. The pressure sensor 8, 9 detects the pressure (P) in the conduit between the restrictor and the corresponding pump. On the other side of the respective restrictor, approximately atmospheric pressure ($P_O$) prevails.

A flow measuring device 12 is positioned between the flow regulators 4 and 5 for measuring the flows to and from the dialyzer 3. Additionally, there are pressure sensors 14 and 15, and a temperature sensor 13, for measuring the temperature of the dialysis fluid.

The flow measuring device 12 comprises two measuring cells, 16 and 17. Measuring cell 16 is arranged to control the set value for the pressure sensor 8 of the constant flow regulator 4 positioned upstream of the dialyzer, while the measurement cell 17 is arranged to control the set value for the pressure sensor 9 in the constant flow regulator 5 positioned downstream of the dialyzer.

Figure 2:
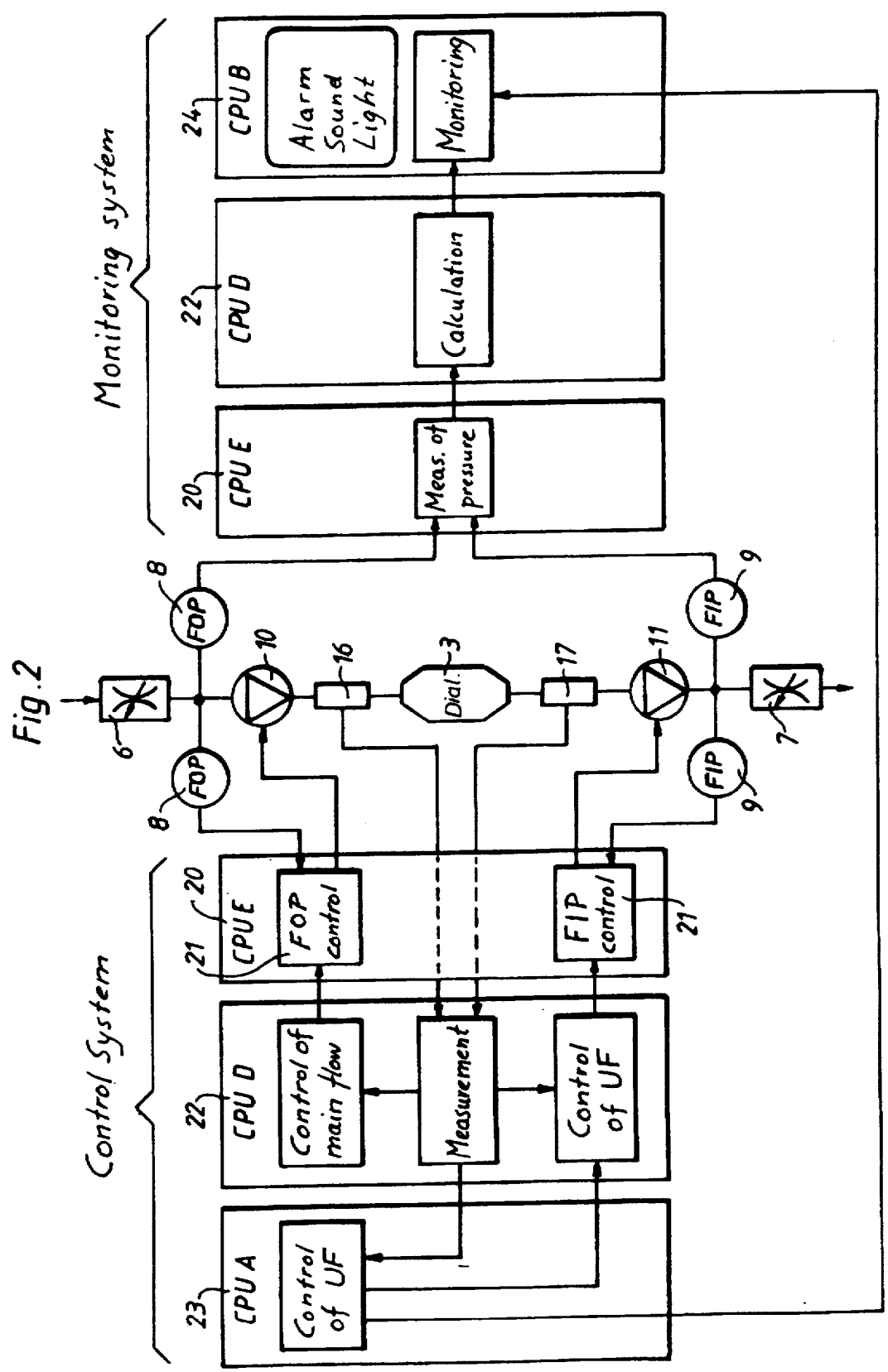
FIG. 2 is a schematic representation of a block diagram which shows the logical construction of the regulating system and monitoring system according to the present invention.

FIG. 2 shows an electrical and logic block diagram of the regulating and monitoring system which is used in the GAMBRO AK-100 and which has been complemented in accordance with the present invention.

On the left side of FIG. 2 a conventional regulating system such as that used in the GAMBRO AK-100 dialysis machine is shown. The above described arrangements such as the restrictor 6, the pump 10, the measuring cell 16, the dialyzer 3, the measuring cell 17, the pump 11 and the restrictor 7 are shown in the middle, and are positioned in order of the flow direction of the dialysis fluid. Additionally, a first pressure sensor 8 is shown, denoted FOP, and a second pressure sensor 9, denoted FIP.

The pressure sensors, 8 and 9, send electrical signals to a microprocessor 20 denoted CPU E. A block 21 in the CPU E takes care of regulation of the pumps 10 and 11, respectively, so that the pressure detected by the pressure sensors 8 and 9, respectively, corresponds with a respective set value. The set value is calculated in a second microprocessor 22 denoted CPU D on the basis of measured signals from the measuring cells, 16 and 17, and dependent on the set desired values of the main flow and ultrafiltration.

Thus, there is a first control loop for regulating the pumps 10 and 11, respectively, via the pressure sensors 8 and 9, respectively, and the block 21. Additionally, there is a second control loop from the measuring cells, 16 and 17, to the microprocessor 22, CPU D, which sends the set values to the block 21 for controlling the first control loop and, along with this, the respective pumps. The first control loop has a small time constant while the second control loop has a large time constant.

The second microprocessor 22, CPU D, calculates the accumulated ultrafiltration volume. A third microprocessor 23, CPU A, regulates the ultrafiltration. The calculated ultrafiltration volume is fed to a fourth microprocessor 24, CPU B, where the calculated value is compared to a set value. If the difference from the set value is too large, alarm signals are produced, such as sound and/or light signals.

According to the present invention the measurement signals from the pressure sensors 8 and 9 are also used to calculate the flow through the throttle devices, 6 and 7, with the help of the aforementioned equation. The measurement signals from the pressure sensors, 8 and 9, are already in the microprocessor 20, CPU E. These measured values are fed to the microprocessor 22, CPU D, where calculation of the flows through respective throttle devices, 6 and 7, occurs. The difference between these calculated flows is accumulated and fed to the microprocessor 24, CPU B, for comparison with the value of the accumulated ultrafiltration volume calculated in the microprocessor 23, CPU A. The calculated flows can also be used for comparison with the measured signals from the measuring cells, 16 and 17, in order to check that these cells are working correctly.

The aforementioned equation comprises three parameters, namely the exponential n, the coefficient k and the back pressure $P_O$.

The exponential n depends on the geometry of the restrictor device. In the GAMBRO AK-100 dialysis machine a restrictor is used which consists of several radial inlet flows to a small axial channel. The channel terminates in a well rounded edge. We have found that the exponential n for such a restrictor is very close to 2. Thus n=2 is preferably used in accordance with the present invention. For other types of restrictor devices or throttle devices, n is approximated to particular values which can be determined experimentally. According to the present invention the value of n is not changed during use.

The coefficient k is determined in advance prior to using the dialysis machine in a separate calibration step. The coefficient $k_{kal}$ obtained in the calibration step is checked before and during dialysis, but is not normally adjusted during dialysis. If the coefficient changes value during the dialysis treatment this is treated as a serious error which should be sorted out.

The back pressure $P_O$ constitutes a measured value of the pressure which exists on the other side of the throttle device. The back pressure can be different depending on the degree of filling of a vessel which is used in the first part of the dialysis machine, or it can depend on the height of a drain where the dialysis fluid is discharged from the machine. Pressure variations can also be present for example with air build-up in the drain tube. The back pressure $P_O$ comprises a conglomeration of the flow resistances which are present from atmospheric pressure to the restrictor, and therefore includes not only the static pressure but also height differences and dynamic pressure such as flow resistances in the tubes, valve devices and other components.

The back pressure $P_O$ is determined and/or is measured both during the calibration step as well as during start-up of the dialysis device and with intermittently performed estimations during the dialysis treatment. The back pressure $P_O$ is used in order to adapt the equation so that the difference between the actual flow and the flow calculated according to the equation is minimal.

CALIBRATION

During calibration, the dialysis machine is coupled such that the dialyzer is shunted and the same dialysis fluid passes through both restrictors and both measuring cells. The flow through the dialysis machine is set for two different values and the pressure readings of the pressure sensors are registered. The flow can be measured with the help of an outer measurement device, such as by measurement of the volume which is passed during a certain time, whereby the measuring cells can be calibrated at the same time. Alternatively, the measured value from the measuring cells 16 and 17 can be used as a measurement of the flow. The relationship between pressure and flow is thus determined at two different measuring points. The coefficient $k_{kal}$ and back pressure $P_{Okal}$ are calculated according to the formula set forth below for each restrictor by using the four obtained measured values:

$$k_{kal} = \frac{P_1 - P_2}{Q_1^2 - Q_2^2} \quad P_{Okal} = \frac{P_2 Q_1^2 - P_1 Q_2^2}{Q_1^2 - Q_2^2}$$

In order to obtain high accuracy for the calculation of the coefficient $k_{kal}$, calibration measuring with large flow differences is required. The determination of the coefficient $k_{kal}$ is given priority during calibration.

Additional measurements of the dialysate flow can also be carried out in order to control the calculation of the coefficient $k_{kal}$ as well as for checking that the exponent n can be approximated to the believed value, namely 2.0 in this case.

START-UP

During start-up of the dialysis machine and before actual dialysis, preferably both nominal flow, such as 500 ml/min, and nominal flow minus 50 ml/minute are used. The dialyzer is thereby shunted so that the same flow passes through both restrictors and both measuring cells, respectively. These two flows are used in order to determine the coefficient k and the back pressure $P_O$. Since the difference between both flows is relatively small, determination of the coefficient k is relatively uncertain. The determination of the coefficient k is only used to check that coefficient $k_{kal}$ lies within the given limits. Depending on which nominal flow it is intended to use, there are different sizes of restrictors in the dialysis machine. Nominal flow can be e.g. 300, 500 or 700 ml/minute. If the determined coefficient k does not lie within the given limits for any of these restrictors, an error signal is emitted. The cause can be that the flow meter and/or the restrictor require cleaning.

The back pressure $P_O$ can be determined with great certainty. The back pressure $P_O$ thus obtained is compared with the calibrated pressure $P_{Okal}$ and has to be within given limits.

The temperature and the conductivity for the dialysis machine are thereafter regulated, and an estimation is then carried out.

ESTIMATION

During the dialysis process the dialyzer is decoupled at regular intervals by means of the shunt arrangement. During estimation a check is made of how much the back pressure $P_O$ for the second restrictor 7 has changed. The interval between estimations is determined by means of a reasonable estimation with respect to how large the total volume error can be until the next estimation, and is normally about 30 minutes. During estimation, the back pressure $P_O$ for the second restrictor 7 is corrected to be in accordance with the measured values from the corresponding measuring cells.

During estimation the coefficient $k_{kal}$ can also be checked by the use of two different flows, for example nominal flow as well as nominal flow minus 50 ml/minute. Apart from this, the error in the coefficient $k_{kal}$ can, to a certain extent, be compensated by correction of the back pressure $P_O$.

MONITORING DURING TREATMENT

The measured values from the pressure sensors are fed continually to the regulating computer from the pressure sensors. With the help of the coefficient $k_{kal}$ and the back pressure $P_O$ the flows through the restrictors can be calculated continually. Such calculations occur in the regulating computer, only at predetermined intervals depending on the calculation capacity of the regulating computer and dependent on the desired accuracy of the monitoring of the ultrafiltration rate. The difference between the calculated flows is accumulated in order to obtain a calculated ultrafiltration volume which is compared with the accumulated ultrafiltration volume which has been calculated in a conventional manner by the regulating computer. If this difference exceeds a predetermined value, a technical error is indicated. The limit can be set such that the volumetric difference is allowed to be larger at the end of the treatment than at the start of the treatment. Such limit can be a percentage error or an absolute error.

The monitoring of the function of the ordinary measuring cells has been described above by utilizing the calculated flow. It is possible to completely replace the measuring cells with flow measurement according to the present invention, whereby the calibration and/or start-up occurs for example by measuring the volume per unit of time. Monitoring can thereby occur by means of the measuring cells or with separate flow meters of the volumetric type, or in other ways, such as described in Swedish Patent Application No. 94.04245-4.

As appears from the drawings, the pump of each constant flow device is positioned closer to the dialyzer than the restrictor. This is of importance, since the control feed-back loop is across the pump. The feed-back loop includes amplification means, which very carefully and rapidly counterfeits every tendency to alter the pressure between the pump and restrictor. The arrangement can be compared to a transistor connected in a common emitter coupling, where the base-emitter-junction is the restrictor and the base-collector-junction is the pump. By having a large pressure drop across the restrictor, further advantages are obtained. By having the other side of the restrictor connected to a constant back-pressure, such as atmospheric pressure, further advantages are obtained.

As an alternative to using available microprocessors, a separate measuring computer especially for monitoring can be used according to the present invention.

Other alternatives are the use of the same computer CPU D 22 for both regulating and monitoring in order to improve the quality of the flow measurement.

Additionally the measuring cells can of course be of a different type than those described above, for example such as those disclosed in U.S. Pat. No. 4,827,430.

The invention has been described above with reference to the preferred embodiments of the invention shown in the drawings. It is however clear that the invention can be modified in many ways without departing from the inventive idea. Modifications which would be obvious for the skilled man are thus intended to be included within the framework of the invention.

We claim:

1. In a dialysis machine comprising a dialyzer, apparatus for monitoring flow through said machine comprising first constant flow means for feeding a dialysis fluid to said dialysis fluid from said dialyzer, said first constant flow means comprising a first throttle, a first pump, and a first pressure sensor for sensing the pressure in said dialysis fluid between said first throttle and said first pump, said second constant flow means comprising a second throttle, a second pump, and a second pressure sensor for sensing the pressure in said dialysis fluid between said second throttle and said second pump, pump control means for controlling said first and second pumps in order to maintain a substantially constant flow of said dialysis fluid through said first and second pumps based upon said pressures measured by said first and second pressure sensors, first flow measurement means for measuring the flow of said dialysis fluid into said dialyzer, and second flow measurement means for measuring the flow of said dialysis fluid out of said dialyzer, said apparatus also comprising calculating means for calculating the flow rates of said dialysis fluid into and out of said dialyzer based upon the formula $P-P_O=k*Q^n$, wherein P comprises said pressure in said dialysis fluid between said first throttle and said first pump and said pressure in said dialysis fluid between said second throttle and said second pump, $P_O$ comprises the pressure in said dialysis fluid on the opposite side of said first throttle and said second throttle, k comprises a characteristic coefficient for said first throttle and said second throttle, Q comprises the flow of said dialysis fluid through said first throttle and said second throttle, and n comprises a characteristic exponent for said first throttle and said second throttle, calibration means for calibrating the values of said k and $P_O$ prior to use of said dialysis machine based upon the flow of said dialysis fluid measured by said first and second flow measurement means, and for calibrating the value of said $P_O$ without calibrating any value of said k during said use of said dialysis machine, and decoupling means for decoupling said dialyzer from said apparatus whereby said value of $P_O$ can be calculated during use of said dialysis machine based upon said flow of said dialysis fluid as measured by said first and second flow measurement means.

2. The apparatus of claim 1 wherein said first pump is arranged to be disposed closer to said dialyzer than said first throttle, and said second pump is arranged to be disposed closer to said dialyzer than said second throttle.

3. The apparatus of claim 1 including temperature measuring means for measuring the temperature of said dialysis fluid whereby the values of said k and said $P_O$ can be corrected based upon the temperature of said dialysis fluid measured by said temperature measuring means.

4. A method for monitoring the flow of a dialysis fluid through a dialysis machine having a dialyzer comprising: first constant flow means for feeding said dialysis fluid to said dialyzer, second constant flow means for withdrawing said dialysis fluid from said dialyzer, said first constant flow means comprising a first throttle, a first pump, and a first pressure sensor for sensing the pressure in said dialysis fluid between said first throttle and said first pump, and said second constant flow means comprising a second throttle, a second pump, and a second pressure sensor for sensing the pressure in said dialysis fluid between said second throttle and said second pump, said method comprising feeding said dialysis fluid to said dialyzer by said first constant flow means, withdrawing said dialysis fluid from said dialyzer through said second constant flow means, maintaining a substantially constant flow of said dialysis fluid through said first and second pumps based upon said pressures measured by said first and second pressure sensors, measuring the flow of said dialysis fluid into said dialyzer, measuring the flow of said dialysis fluid out of said dialyzer, calculating the flow rates of said dialysis fluid into and out of said dialyzer based upon the formula $P-P_O=k*Q^n$, wherein P comprises said pressure in said dialysis fluid between said first throttle and said first pump and said pressure in said dialysis fluid between said second throttle and said second pump, $P_O$ comprises the pressure in said dialysis fluid on the opposite side of said first throttle and said second throttle, k comprises a characteristic coefficient for said first throttle and said second throttle, Q comprises the flow of said dialysis fluid through said first throttle and said second throttle, and n comprises a characteristic exponent for said first throttle or said second throttle, calibrating the value of said k and $P_O$ prior to use of said dialysis machine based upon the flow of said dialysis fluid measured into and out of said dialyzer, and for calibrating the value of said $P_O$ without calibrating any value of said K during said use of said dialysis machine, and decoupling said dialyzer from said apparatus whereby said value of $P_O$ can be calculated during use of said dialysis machine based upon said flow of said dialysis fluid into and out of said dialyzer.

5. The method of claim 4 wherein the step of calibrating the values of said k and said $P_O$ prior to said machine use comprises feeding an increased flow of fluid through at least one of said first and second throttles, measuring said pressure of at least one of said first and second pressure sensors during said increased flow, and measuring the flow of said dialysis fluid into or out of said dialyzer during said increased flow.

6. The method of claim 4 wherein the step of calibrating the value of said $P_O$ during said machine use comprises feeding at least a first increased large flow and a second increased large flow differing from said first increased large flow to at least one of said first and second throttles, measuring the flow into or out of said dialyzer during said first and second increased flows, and calculating the value of said $P_O$ based thereon.

7. The method of claim 4 including calculating accumulated ultrafiltration in said dialysis machine based upon said flow of said dialysis fluid into and out of said dialyzer and said measured flows of said dialysis fluid through said first and second throttles.

8. The method of claim 9 including approximating the value of said n to a predetermined value.

9. The method of claim 8 wherein said predetermined value comprises 2.

10. The method of claim 4 including initially proximating the value of said $P_O$ to a constant predetermined value.

11. The method of claim 2 wherein said constant predetermined value comprises atmospheric pressure.

* * * * *

UNITED STATES PATENT AND TRADEMARK OFFICE
CERTIFICATE OF CORRECTION

PATENT NO. : 5,792,367
DATED : August 11, 1998
INVENTOR(S) : Mattisson et al.

It is certified that error appears in the above-identified patent and that said Letters Patent is hereby corrected as shown below:

Delete "$P-P_0 = k^*Q^n$" wherever it appears throughout the patent and substitute -- $P - P_0 = k * Q^n$ --

Column 9, lines 32, delete "a dialysis fluid to".

Column 9, line 33, "from" should read --to--

Column 9, line 33, after "dialyzer," insert --second constant flow means for withdrawing said dialysis fluid from said dialyzer,--

Column 10, line 47, "K" should read --k--.

Column 11, line 6, "9" should read --4--.

Column 12, line 5, "2" should read --10--.

Signed and Sealed this

Nineteenth Day of January, 1999

Attest:

*Attesting Officer*

*Acting Commissioner of Patents and Trademarks*